United States Patent [19]
Li

[11] Patent Number: 5,259,395
[45] Date of Patent: Nov. 9, 1993

[54] PACEMAKER LEAD WITH EXTENDABLE RETRACTABLE LOCKABLE FIXING HELIX

[75] Inventor: Hong Li, Irvine, Calif.

[73] Assignee: Siemens Pacesetter, Inc., Sylmar, Calif.

[21] Appl. No.: 821,107

[22] Filed: Jan. 15, 1992

[51] Int. Cl.⁵ .............................................. A61N 1/05
[52] U.S. Cl. .................................... 607/131; 128/642; 607/127
[58] Field of Search .............................. 128/784–786, 128/642, 419 P

[56] References Cited

U.S. PATENT DOCUMENTS

| | | | |
|---|---|---|---|
| 4,628,943 | 12/1986 | Miller | 128/785 |
| 4,667,686 | 5/1987 | Peers-Travarton | 128/785 |
| 4,886,074 | 12/1989 | Bisping | 128/785 |
| 4,953,564 | 9/1990 | Berthelsen | 128/419 P X |
| 5,020,545 | 6/1991 | Soukup | 128/785 |
| 5,152,299 | 10/1992 | Soukup | 128/785 |

FOREIGN PATENT DOCUMENTS 3230081 2/1984 Fed. Rep. of Germany.
3712082 10/1988 Fed. Rep. of Germany ...... 128/785

Primary Examiner—Lee S. Cohen
Assistant Examiner—Jeffrey R. Jastrzab
Attorney, Agent, or Firm—Malcolm J. Romano

[57] ABSTRACT

A body implantable lead including a sheath, an electrode sleeve secured at a distal end of the sheath, a rotor body positioned within the sleeve, a fixing helix secured to a distal end of the rotor body, a torsion spring secured to a proximal end of the rotor body, and a rotation guide formed between the electrode sleeve and the rotor body which includes a helical groove formed on either the rotor body or the electrode sleeve and at least one guide pin formed on the electrode sleeve or the rotor body, respectively.

22 Claims, 1 Drawing Sheet

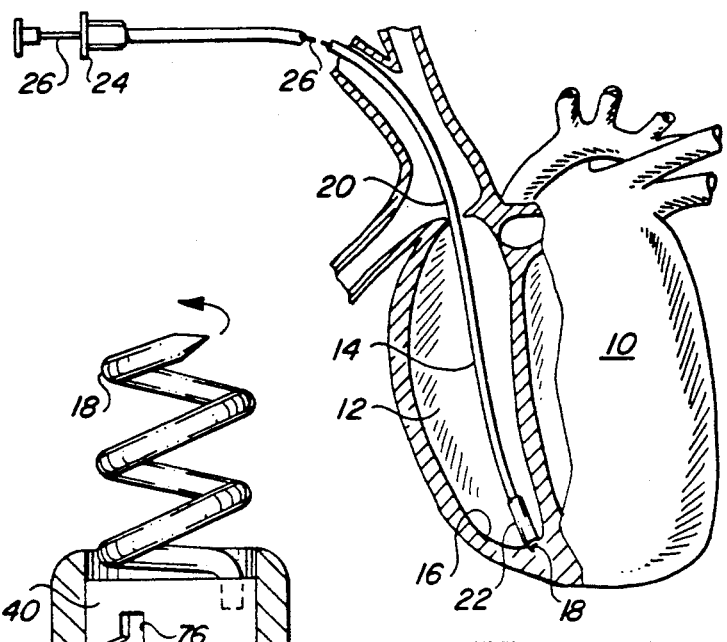
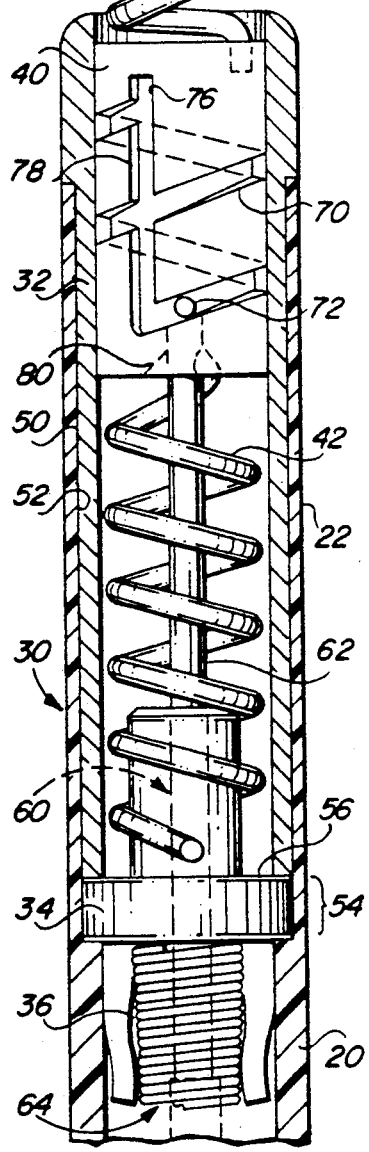
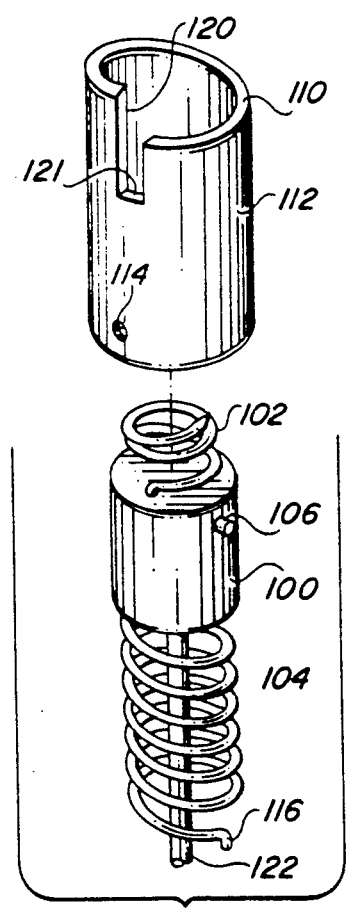
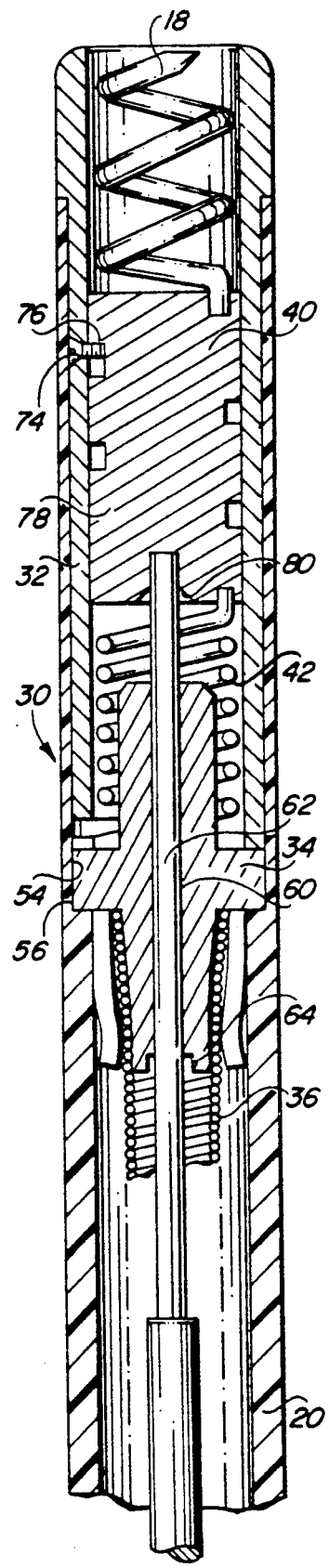
FIG-1
FIG-2
FIG-4
FIG-3

PACEMAKER LEAD WITH EXTENDABLE RETRACTABLE LOCKABLE FIXING HELIX

BACKGROUND OF THE INVENTION

The present invention generally relates to body implantable cardiac lead assemblies. More specifically, the invention relates to implantable leads with fixing helixes. Yet more specifically, the invention relates to implantable leads with means for actuating the fixing helix to automatically screw into body tissue.

Numerous types of implantable lead assemblies are known for use with cardiac pacemakers having different types of structures for fixing the tip of the lead to cardiac tissue. In one type of lead assembly, a fixing helix is positioned at the distal end of an implantable lead so that the lead can be attached to body tissue, such as the heart, by appropriate rotation of the helix such that the helix screws into the body tissue. Various structures for rotating the helix have been devised.

U.S. Pat. No. 4,217,913 discloses an implantable endocardial lead assembly with a protected, extendable, fixing helix. The fixing helix is extendable out of the distal end of the lead assembly through a tissue covering the lead. In one embodiment, the lead is provided with a spring loaded stylet such that the helix can be automatically driven by the spring in rotating fashion to automatically engage and secure into heart tissue. A threaded arrangement between the stylet and the outer casing of the lead ensures that the helix rotates only a predetermined distance.

In operation, prior to insertion of the stylet, a knob is wound a number of turns to store rotational energy in a spring. Upon release, the spring rotates a rotor body an approximate number of turns. A compressor spring assists in imparting forward rotational movement and to prevent backlash of the rotor body.

U.S. Pat. No. 4,649,938 discloses an implantable lead assembly having an extendable/retractable fixing helix. The helix extends beyond the tip of the lead only upon the application of an external force by a stylet on a carrier bobbin on which the helix is mounted. Otherwise, biasing means also positioned within the lead, urges the fixing helix to a retracted position within the distal tip of the lead assembly. Rotation of the helix is effected manually. The carrier bobbin and lead are provided with complementary octagonal shapes, much like a socket wrench and not respectively so that rotation of the lead will cause rotation of the bobbin.

U.S. Pat. No. 4,858,623 discloses an active fixing mechanism for the lead assembly of an implantable endocardial lead. The active fixing mechanism includes a tissue stimulating electrode with a rigid hook for engaging tissue, which hook is pivotally fastened to the lead in the vicinity of the electrode. The tip of the hook is normally resiliently urged into a recess and lead adjacent to the electrode. A mechanism is coupled to the lead to permit the normal bias of the hook tip to be selectively overcome to position the hook outwardly of the lead. In this position, the hook is deployed to engage tissue in the vicinity of the electrode. The force applied to deploy the hook may be removed to allow the hook to move back into the recess under the normal bias. Sufficient force supplied to the hook while deployed along the axis of the lead, will cause the hook to assume a position beyond the distal end of the lead, in which it is precluded from engaging tissue.

U.S. Pat. No. 4,886,074 discloses an implantable endocardial lead assembly with an extendable helix and electrode wherein the lead assembly has an electrode head which includes a fixing helix for implantation into tissue, a prelocking spring that upon release causes the helix to rotate, as well as a releasable blocking mechanism that prevents rotation. The electrode head includes all of the elements required for the blocking function of the mechanism and can be released by axial movement of the fixing helix or a connector block associated with the helix.

In an embodiment, all of the elements of the blocking mechanism are directly attached to the fixing helix, the connector block, the electrode lead, or the insulating sheath, such that the release of the block is accomplished by axial movement of the helix and the connector block from the area of the blocking mechanism at the electrode head or the insulating sheath. Small axial forces are sufficient to release the blocking mechanism and axial movement of the fixing spiral or the connector block can be accomplished either mechanically, hydraulically, or pneumatically.

It is discussed that mechanical release blocking of the mechanism can be accomplished by means of an axial shifting movement of a stylet.

In one embodiment, the helix is secured to a rotatable connector block which itself is positioned within the sleeve. A pin protruding from the sheath engages a small slot in the connector block to prevent rotation. However, the insertion of a stylet will cause the block to move sufficiently axially such that the pin is disengaged and then the connector block and the helix secured thereto rotate under the influence of a stored torsional force provided by a prestressed spring.

U.S. Pat. No. 4,924,881 discloses an implantable endocardial lead with a retractable fixing helix wherein the fixing helix comprises a sharpened helix which can be repeatedly both retracted within a distal end of the lead and displaced outside the lead. A threaded stylet passes through a sheath from a proximal end of the lead to the distal end of the lead, where the threaded stylet is screwed into a piston supporting the helix. When the helix is in an exposed position, torque can be transmitted from the proximal end of the lead through the distal end to the piston and then to the helix to screw the helix into the endocardial tissue.

German OS 32 30 081 discloses a lead assembly with a fixing helix arrangement designed for use With a heart pacemaker including a catch which locks the helix into an extended position.

The disclosures of all of these patents are incorporated herein by reference.

SUMMARY OF THE INVENTION

The present invention provides an improved body implantable lead assembly having a fixing helix that can be actuated to automatically freely rotate thereby to attach the lead to body tissue. To this end, the invention provides a helix secured to a rotor body which itself is positioned within the lead, prestressed torsion means secured to the rotor body, and guide means formed on the rotor body and the lead comprising a helical groove and a pin that engages the helical groove so as to guide the rotor body through a predetermined number of turns and along a predetermined axial path.

In an embodiment, the invention provides an implantable lead including an electrically insulating sheath or lumen, an electrode sleeve positioned at a distal end of the sheath, the electrical sleeve contained in the sheath terminating in an exposed electrode, a rotor body positioned within the sleeve carrying a fixing helix, a nonrotatable fixed block, a torsion spring secured between the fixed block and the rotor body, and guide means for guiding the rotor body through a predetermined number of turns and along a predetermined axial distance comprising a helical groove and a guide pin that engages the groove so that the fixing helix is moved from a position within the sheath to an exposed position beyond the end of the sheath so as to be engageable with cardiac tissue and thereby to hold the electrode securely in contact with the cardiac tissue.

In a preferred embodiment, the helical groove is formed about an outer surface of the rotor body and the guide pin extends from the sleeve.

In an embodiment, the helical groove is formed about an inner surface of the sleeve and the guide pin is formed on the rotor body.

In an embodiment, the surface on which the helical groove is formed includes longitudinal grooves that extend beyond opposite ends of the helical groove so as to provide catches within which the guide pin rests to prevent rotation of the helix.

In an embodiment, the fixed block includes an axial bore so that a stylet inserted therethrough can be used to axially displace the rotor body a distance sufficient to cause the guide pin to engage the helical groove and thereby allow the rotor body to rotate freely under the influence of the torsion spring.

These and other features of the invention will become clear below in the following detailed description of the presently preferred embodiments and accompanying drawings.

DESCRIPTION OF THE DRAWINGS

FIG. 1 illustrates a heart with a portion cut away to reveal an implantable lead assembly secured therein to a wall of the heart.

FIG. 2 illustrates in partial sectional view the implantable lead assembly of FIG. 1 with a fixing helix in extended position;

FIG. 3 illustrates in sectional view the implantable lead assembly of FIG. 2 with the fixing helix in retracted position; and FIG. 4 illustrates in exploded view a portion of an alternate lead assembly.

DETAILED DESCRIPTION OF THE PREFERRED EMBODIMENT

In accordance with the invention, a body implantable lead is provided with a fixing helix that can be actuated to automatically and freely rotate a predetermined number of turns and along a predetermined axial distance to attach to body tissue. To this end, cooperating guide means are formed on the rotor body and the lead comprising a helical groove and a guide pin that engages the helical groove. With reference to the figures, implantable leads embodying these features will be described.

In FIG. 1, there is illustrated a heart 10 into the left ventricle 12 of which is inserted a body implantable lead 14 of the endocardial lead type. The lead 14 is attached to an interior wall 16 of the heart 10 by means of a fixing helix 18 that is screwed, corkscrew style, into the wall 16.

As further illustrated, the lead 14 also includes an insulating sheath 20 interconnecting a distal electrode end 22 secured adjacent to the interior wall 16 and a proximal end 24 to which can be attached a source of electrical energy such as a pacemaker. In FIG. 1 a stylet 26 is illustrated as being inserted within the sheath 20, for purposes better explained below, such as for providing rigidity to the sheath 20 during insertion of the lead 14 into the heart 10.

An assembly 30 of the lead 14 is illustrated in greater detail in FIGS. 2 and 3.

As illustrated in FIGS. 2 and 3, the body implantable lead 14, for providing stimulating electrical signals to body tissue, for example the heart, preferably is provided with the sheath 20 and an electrically conductive electrode sleeve 32 secured in the distal end of the sheath 20. As is further illustrated, other major components of the lead 14 include a fixed block 34, an electrical conductor 36 interconnecting the source of electrical energy and the electrode sleeve 32, a rotor body 40, a torsion spring 42, and the fixing helix 18.

It can be appreciated that the sleeve 32 is electrically connected to the proximal end of the lead 14 by means of the helical conductor 36 which is electrically insulated from the body tissue by means of the insulating sheath 20. So that the conductor 36 is electrically connected to the sleeve 32, the fixed block 34 preferably also is electrically conducting.

The sleeve 32 and the sheath 20 include cooperating outer rabbet 50 and inner rabbet 52, respectively, such that a portion of the sleeve 32 extends into the interior of the sheath 20 and an outer surface of the sleeve 32 and an outer surface of the sheath 20 preferably form a smooth continuous surface. The distal tip of the lead 14, however, is formed by the exposed portion of the sleeve 32 so that good electrode contact can be had between the sleeve 32 and the body tissue.

As illustrated, however, the longitudinal length of the rabbet 50 of the sleeve 32 is not as extensive as the rabbet 52 of the sheath 20 to provide a gap 54 within which is captured an annular flange 56 of the fixed block 34. Because the annular flange 56 of the fixed block 34 is captured in this gap 54, the block 34 is secured in fixed relation with respect to the sleeve 32 and the sheath 20.

For purposes that will become clearer below, the fixed block 34 includes a central bore 60 extending therethrough, through which a relatively small diameter stylet 62 can be inserted. Further, the fixed block 34 includes a counterbore 64 located on the proximal end of the fixed block 34. The counterbore 64 is shaped to receive the distal end of a relatively large diameter stylet, not illustrated in FIGS. 2 and 3. It can be appreciated that the relative large diameter stylet cannot be inserted through the central bore 60.

The counterbore 64 is provided to accommodate the relatively large diameter stylet which is used during implantation of the lead 14 through, for example, a vein, such is in the case of the stylet 26 of FIG. 1. The relatively large diameter stylet provides rigidity to the lead 14 to thereby assist in the placement of the distal end of the lead 14 adjacent to the position at which it will be attached to body tissue. The smaller central bore 60 is provided to accommodate only the relatively small diameter stylet 62 that is used after the lead 14 has been positioned for attachment. The relatively small diameter stylet 62 is used to contact the rotor body 40 to apply an external distally directed force thereto to axially displace the rotor body 40 to allow it to freely rotate as will be explained.

As illustrated, the rotor body 40 is cylindrically shaped and preferably includes a helical groove 70 that includes a predetermined number of turns about the outer curved surface of the rotor body 40. The sleeve 32 then preferably includes a guide member in the form of a fixed guide pin 72 (FIG. 2) or removable guide screw 74 (FIG. 3) that engages the helical groove 70. It can be appreciated that during rotation of the rotor body 40, the guide pin 72 or guide screw 74 will engage the helical groove 70 to guide or cam the rotor body 40 through a predetermined number of rotations. Further, because of the axial or longitudinal dimension of the helical groove 70, the guide pin 72 or guide screw 74 will also guide the rotor body 40 through a predetermined axial path toward the distal end of the sleeve 32.

As illustrated most clearly in FIG. 2, a longitudinal groove 78 cuts through the helical groove 70 and terminates on the distal end in a catch 76. This catch 76 locks the guide pin 72 or guide screw 74 so as to prevent rotation of the rotor body 40 when such rotation is not desired.

On its proximal end, the rotor body 40 includes a small recess or bore 80 constructed to receive the distal end of the relatively smaller diameter stylet 62. The recess 80 and stylet 62 preferably are constructed to engage and cooperate much like a screwdriver and bolt or screw. When appropriate, the stylet 62 can be used to impart torsion to the torsion spring 42 and/or to unscrew fixing the helix 18 from the body tissue.

The torsion spring 42 is secured on its proximal end to the fixed block 34 and on its distal end to the proximal end of rotor body 40. The torsion spring 42 can be prestressed or prewound so that it exerts a rotational bias on the rotor body 40. The prestressing can be factory preset or provided by manual on-site preparation by appropriate rotation of the rotor body 40. e.g., by the stylet 62. To insure that sufficient rotational bias is provided, however, it is preferred to have the torsion spring 42 prewound or prestressed at a factory controlled setting. The fixing helix 18 is secured on a distal end of the rotor body 40 and, as will become apparent, upon rotation of the rotor body 40 will extend from the distal end of the sleeve 32 to secure into the body tissue.

In operation, as described above, at first, the relatively larger diameter stylet is inserted into the sheath 20 until the distal end of the relatively large diameter stylet is captured within the counterbore 64 of the fixed block 34. The stylet provides rigidity to the lead 14 and the lead 14 is then introduced through a vein until it is positioned for attachment to tissue. eg, adjacent to the inner wall 16 of the heart 10. At that time, the relatively large diameter stylet is removed from the sheath 20 and the relatively small diameter stylet 62 is introduced through the central bore 60 of the fixed block 34. The distal end of the latter stylet is received within the recess 80 in the proximal end of the rotor body 40 and upon the application of a sufficient distally directed axial force, the rotor body 40 is caused to move axially toward the distal end of the sleeve 32.

The torsion spring 42 preferably is prestressed so that the rotor body 40 is biased to rotate. However, due to the stressing of the torsion spring 42, an axial force is also introduced that pulls the rotor body 40 toward the proximal end of the lead 14. As such, the guide pin 72 or guide screw 74 will initially be engaged within the catch 76 at the distal end of the helical groove 70.

Upon the application of the axial force by the relatively small diameter stylet 62, the rotor body 40 will move axially toward the distal end of the lead 14 and the guide pin 72 or guide screw 74 will travel in the proximal direction relative to the rotor body 40. Once the guide pin 72 or guide screw 74 reaches the distal end of the helical groove 70, the rotational bias of the spring 42 will cause the rotor body 40 to rotate. At that time, if the axial force applied by the relatively smaller diameter stylet is maintained, the rotor body 40 will freely rotate until the guide pin 72 or guide screw 74 reaches the proximal end of the helical groove 70. It can be appreciated that due to the rotation of the rotor body 40, the fixing helix 18 secured thereto will also rotate and will screw into the tissue. It can also be appreciated that due to the helical groove 70 and guide pin 72 or guide screw 74 arrangement, the rotor body 40 will rotate through a predetermined number of turns and will travel axially only a predetermined distance.

Appropriate construction of the relationship between the fixing helix 18 and the rotor body 40 will result in the rotor body 40 terminating its rotation such that the distal end thereof is flush with the distal end of the sleeve 32 when the fixing helix 18 is fully introduced into the body tissue. Of course, any number of turns can be provided in the helical groove 70, the actual number being limited by, among other things, the size of the lead 14 and the length of the rotor body 40. However, a number of turns of two (2) should provide good results.

Should the fixing helix not be secured into the body tissue after rotation, release of the axial force on the rotor body 40 by the relatively smaller stylet 62 will permit the guide pin 72 or guide screw 74 to travel in the distal direction along the longitudinal return groove 78 relative to the rotor body 40. Once the guide pin 72 or guide screw 74 returns to the catch 76, another attempt to rotate the fixing helix 18 can be undertaken, depending upon the torsional bias remaining in the torsion spring 42.

It is preferred that the torsion spring 42 be prewound so as to be imparted with a torsional bias sufficient to enable the rotor body 40 to rotate through ten (10) full rotations. Since it is preferred that the helical groove 70 have at least two (2) turns, the torsion spring 42 preferably is prestressed for five (5) actuations of rotation.

It can be appreciated that the force exerted by the fixing helix 18 in screwing into the body tissue can be controlled by the amount of axial force exerted by the smaller diameter stylet 62. With slight axial force, the guide pin 72 or guide screw 74 will cam along the walls of the groove 70. In camming, frictional forces on the distal side of the groove 70 will retard the progress of the pin 72 or screw 74 through the groove 70. However, further axial force exerted on the rotor body 40 by the stylet 62 will reduce the amount of the frictional forces, thereby allowing more of the torsional force of the torsion spring 42 to be translated into rotational movement of the rotor body 40. Further, excessive axial force by the stylet 62 will cause the pin 72 or screw 74 to engage against the opposite or proximal side of the groove 70, thereby again producing frictional forces on the rotor body 40.

In addition to the foregoing, it is also possible to realize an embodiment of the invention wherein a helical groove is provided on the inner surface of the sleeve and one or more guide pins are provided on the rotor body. This would merely be a reversal of parts of the above-described embodiment. However, it is easier to form the groove 70 in the rotor body 40 than in the sleeve 32, and thus the illustrated embodiment is preferred.

In FIG. 4, however, there is illustrated an alternate arrangement for imparting controlled rotational movement to a rotor body in an implantable lead. In FIG. 4, a rotor body 100 is illustrated as including a fixing helix 102 secured on a distal end of the rotor body 100 and a torsion spring 104 secured on a proximal end of the rotor body 100. The rotor body preferably is cylindrically shaped.

As also illustrated, a guide pin 106 extends at a right angle from the outer curved surface of the rotor body 100. The guide pin 106 is designed and positioned to engage and cam on a single turn helical surface 110 of a sleeve 112. In a sense, the arrangement of FIG. 4 is similar to the above-described reversal of parts embodiment, however, in the embodiment of FIG. 4, a helical groove is not provided in, e.g., the sleeve 32 but rather a helical turn is provided on a distal end of the separate second sleeve 112. Of course, the helical surface could be provided as a single turn groove within the sleeve 32.

It can be seen that the sleeve 112 also includes a hole 114 in the sidewall thereof into which engages a proximal end 116 of the torsion spring 104. Thus, twisting of the rotor body 100 relative to the sleeve 112 will impart a stored torque in the torsion spring 104 that can be used to cause the rotor body 100 to rotate upon proper actuation.

To maintain the rotor body 100 in a position with stored torque on the torsion spring 104, a longitudinal groove 120 is provided in the distal end of the sidewall of the sleeve 112. In the preferred embodiment, the distance between the proximal end 121 of the groove 120 and the hole 114 is greater than the distance between the pin 106 on the rotor body 100 and the proximal end 116 of the torsion spring 104. It can be appreciated that the proximally directed axial force exerted by the wound-up torsion spring 104 will cause the guide pin 106 to engage within the groove 120 which, in turn, will capture the pin 106 and prevent the rotor body 100 from rotating. However, upon application of a sufficient distally directed force by, e.g., a stylet 122, the guide pin 106 can be lifted out of the groove 120 and the rotor body 100 will rotate.

It can be further appreciated that the torsion spring 104 will cause the guide pin 106 to return to the groove 120 after one rotation due to the proximally directed axial force exerted by the prestressed torsion spring 104 on the rotor body 100. If the torsion spring 104 is initially provided with a strong tension, then the rotor body 100 can be actuated much like a ball point pen such that upon each push of the stylet 122, the rotor body will undergo a series of singular rotations, upon experience a like series of actuations by the stylet 122. Preferably, the torsion spring 104 is prestressed such that at least ten (10) such rotations can be undertaken.

While a preferred embodiment has been described, modifications and changes may become apparent to those skilled in the art which shall fall within the spirit and scope of the invention. It is intended that such modifications and changes be covered by the attached claims.

What is claimed is:

1. A body implantable lead comprising:
   a hollow insulating sheath with distal and proximal ends;
   an electrode sleeve secured to the distal end of the sheath;
   a rotor body positioned within the electrode sleeve;
   a fixing helix secured to a distal end of the rotor body, the fixing helix movable between fully extended and fully retracted positions;
   a torsion spring secured to a proximal end of the rotor body and to the sheath;
   guide means for guiding the rotor body through a predetermined rotation comprising a helical groove formed in one of the electrode sleeve and the rotor body and at least one guide member engaged in the helical groove formed in the other of the sleeve and rotor body; and
   a longitudinal groove extending between proximal and distal ends thereof that intersects through the helical groove, the longitudinal groove terminating at its distal end in a catch within which the guide member can be captured, the proximal end of the longitudinal groove adapted to permit introduction of the guide member within the helical groove, such that at the fixing helix fully retracted position the guide member is captured and such that at the fixing helix fully extended position the guide member is introduced within the helical groove.

2. The implantable lead, as defined in claim 1, further comprising a fixed block secured to the sheath and to the torsion spring, said fixed block including a central bore through which a stylet can be inserted and a counterbore located on a proximal end of the fixed block, the fixed block being in electrical communication with the electrode sleeve.

3. The implantable lead, as defined in claim 1, wherein the helical groove wraps about a longitudinal axis of the rotor body and includes a distal end and a proximal end 4. The implantable lead, as defined in claim 1, wherein the guide member is a pin fixed to the electrode sleeve.

5. The implantable lead, as defined in claim 1, wherein the guide member is a screw removably secured in the sleeve.

6. A body implantable lead comprising:
   an insulating sheath with distal and proximal ends;
   an electrode sleeve having proximal and distal ends thereof, the electrode sleeve being made of a conductive material disposed at the distal end of the sheath;
   a fixed block electrically connected to the proximal end of the electrode sleeve within the sheath;
   an electrical conductor coupled to the fixed block and the proximal end of the sheath;
   a rotor body extending between proximal and distal ends thereof and disposed within the electrode sleeve, the rotor body including a helical groove formed about an outer surface thereof and a longitudinal groove, that intersects through the helical groove, the longitudinal groove terminating at a distal end thereof within which the guide member can be captured, the longitudinal groove extending to the proximal end of the rotor body to permit introduction of the guide member within the helical groove;
   a torsion spring secured between the fixed bock and the rotor body;
   at least one guide member extending from the electrode sleeve and extending into the helical groove; and
   a fixing helix secured to and extending from said distal end of the rotor body.

7. The implantable lead, as defined in claim 6, wherein the torsion spring can be prestressed so as to bias the rotor body to rotate and to impart an axial force on the rotor body to urge the rotor body in a direction towards the proximal end of the electrode sleeve, such that when the guide member is captured, the rotor body is prevented from rotating under the influence of the bias imparted by the torsion spring.

8. The implantable lead, as defined in claim 7, wherein the fixed block includes a central bore through which a stylet can be inserted to engage against the rotor body to cause the rotor body to move axially sufficiently so that the guide member will engage the helical groove and the rotor body will rotate freely under the influence of the bias imparted by the torsion spring.

9. The implantable lead, as defined in claim 6, wherein the guide member is a pin fixed to the electrode sleeve.

10. The implantable lead, as defined in claim 6, wherein the guide member is a screw removably secured in the electrode sleeve.

11. The implantable lead, as of claim 6, wherein the fixed block includes a central bore and a counter bore and the rotor body includes a recess in its proximal end.

12. An endocardial lead for use with a stylet having a stylet tip, the lead comprising:
an insulating sheath with distal and proximal ends;
an electrically conductive electrode sleeve mounted within the distal end of the sheath;
a fixed body secured within the sheath by the electrode sleeve;
a rotor body positioned within the sleeve;
a spring secured between the fixed body and the rotor body;
a central bore formed in the fixed body for receiving a stylet;
a helical groove formed about an outer surface of the rotor body;
a longitudinal groove formed on the outer surface of the rotor body that intersects through the helical groove;
a guide pin extending from the electrode sleeve to engage the helical groove;
means formed in a proximal end of the rotor body for receiving a stylet tip; and
a fixing helix secured to a distal end of the rotor body.

13. The implantable lead, as defined in claim 12, wherein the guide pin is a pin fixed to the electrode sleeve.

14. The implantable lead, as defined in claim 12, wherein the guide pin is in the form of a screw removably secured in the electrode sleeve.

15. The implantable lead, as defined in claim 12, wherein the helical groove has a proximal end that terminates in said longitudinal groove that extends to a proximal end of the rotor body.

16. An implantable lead, comprising:
a sheath with distal and proximal ends;
an electrode sleeve secured at the distal end of the sheath;
a second sleeve secured within the electrode sleeve;
a rotor body positioned within the second sleeve;
a helical surface formed on a distal end of the second sleeve;
a guide pin extending from the rotor body for engaging the helical surface;
a spring secured between the rotor body and the second sleeve; and
a fixing helix secured on a distal end of the rotor body.

17. The implantable lead, as defined in claim 16 further comprising a longitudinal slot formed in the distal end of the second sleeve and constructed to capture the guide pin therein.

18. The implantable lead, as defined in claim 16, wherein the rotor body includes a recess formed in a proximal end thereof and constructed to receive a stylet therein.

19. A body implantable lead comprising:
a hollow insulating sheath having a distal end adapted for in vivo placement in a heart and a proximal end adapted for percutaneous exposure during implantation;
an electrical conductor extending in and substantially coextensive with said sheath and terminating in an electrode sleeve exposed for contact with cardiac tissue at said distal end of said sheath;
a fixing helix;
a rotor body disposed in said electrode sleeve carrying said fixing helix, normally disposed in a first position with said helix contained within said sleeve, said rotor body and said sleeve forming relatively rotational elements;
a torsion spring engaging said rotor body and biasing said rotor body axially toward said proximal end of said sheath;
a pin carried on one of said relatively rotational elements and a longitudinal groove and a helical groove in the other of said relatively rotational elements, said helical groove having one end terminating in a catch means for said pin for holding said rotor body and said helix in said first position against the bias of said torsion spring, said longitudinal groove having one end terminating in a catch means or said pin for holding said rotor body and said helix in said first position against the bias of said torsion spring, said longitudinal groove extending between proximal and distal ends thereof and intersecting through the helical groove, the proximal end of the longitudinal groove adapted to permit introduction of said pin within the helical groove, the distal end of the longitudinal groove terminating in the catch means; and
means extending through said sheath and manipulable at said proximal end thereof for axially displacing said rotor body to disengage said pin from said catch means to permit said torsion spring to move and rotate said fixing helix, with said pin guided in said helical groove, to a second position extending beyond said distal end of said sheath to engage said cardiac tissue and to hold said electrode sleeve against said cardiac tissue, such that upon release of the extending means said torsion spring urges the rotor body to retract with said pin guided in said longitudinal groove.

20. A body implantable lead comprising:
a hollow insulating sheath with distal and proximal ends thereof;
an electrode sleeve secured to the distal end of the sheath;
a rotor body positioned within the electrode sleeve;
a fixing helix secured to a distal end of the rotor body, the fixing helix and the rotor body together movable between fully extended and fully retracted positions; and guide means for guiding the rotor body through a predetermined rotation, the guide means further comprising:

groove means formed about an outer surface of the rotor body; and a guide member extending from the electrode sleeve and into the groove means, the groove means permitting rotational and transitional movement of the rotor body as the rotor body moves towards the fully extended position, while restricting the rotor body to transitional movement as the rotor body moves from the fully extended to the fully retracted position.

21. The body implantable lead, as defined in claim 20, further comprising a torsion spring secured to a proximal end of the rotor body and the sheath, the torsion spring being prestressed to bias the rotor body to rotate and to impart an axial force for urging the rotor body towards the fully retracted position.

22. The body implantable lead, as defined in claim 21, wherein the sheath includes means for receiving a stylet to engage against the rotor body to cause the rotor body to rotate and translate as the rotor body moves towards the extended position against the force exerted by the torsion spring, and wherein upon removal of the stylet, the torsion spring causes the rotor body to return to the fully retracted position from the fully extended position with the rotor body being restricted to translational movement.

* * * * *